Figure 1:
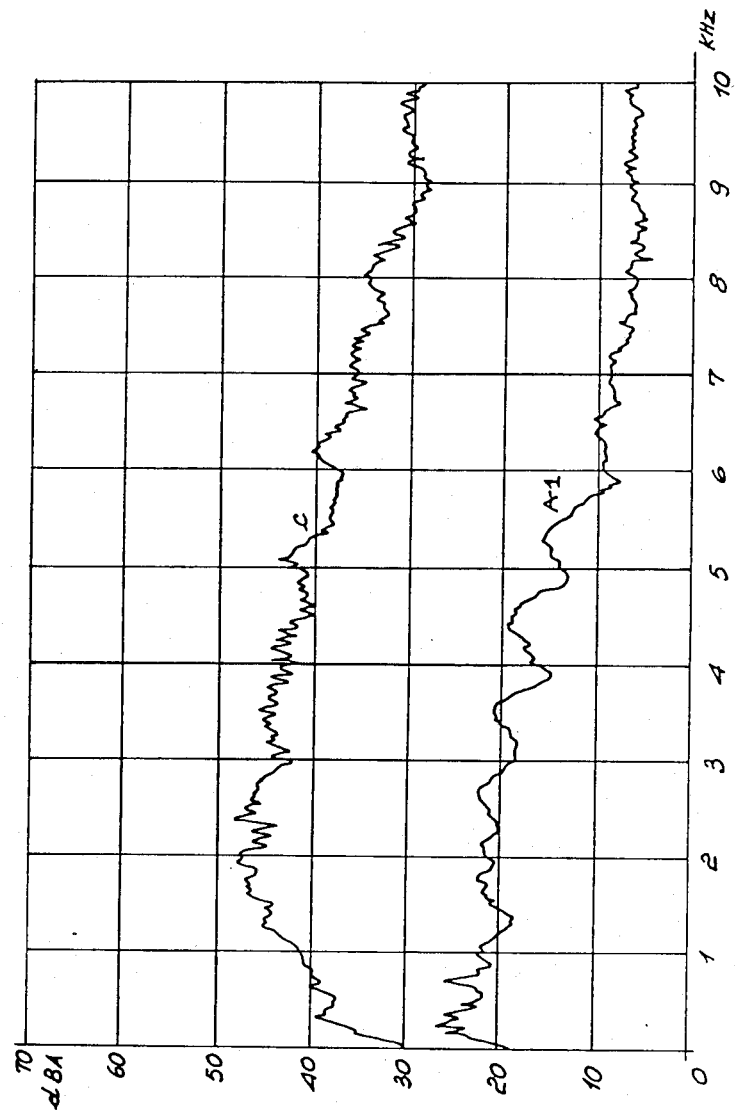

United States Patent [19]

Vietto et al.

[11] Patent Number: 4,687,711

[45] Date of Patent: Aug. 18, 1987

[54] SILENT FILM FOR OSTOMY POUCHES

[75] Inventors: Paolo Vietto, Legnano; Francesco Martini, Rho, both of Italy

[73] Assignee: W. R. Grace & Co., Cryovac Div., Duncan, S.C.

[21] Appl. No.: 825,969

[22] Filed: Feb. 6, 1986

Related U.S. Application Data

[63] Continuation of Ser. No. 587,102, Mar. 7, 1984, abandoned.

[30] Foreign Application Priority Data

May 13, 1983 [IT] Italy .............................. 21109 A/83

[51] Int. Cl.⁴ ............................................ C08L 23/16
[52] U.S. Cl. .................................. 428/515; 428/516; 428/518; 604/374; 525/222
[58] Field of Search ..................... 604/374, 332.5, 339, 604/342, 323, 350, 317; 525/222; 428/515, 516, 518

[56] References Cited

U.S. PATENT DOCUMENTS

| | | | |
|---|---|---|---|
| 3,422,055 | 1/1969 | Matoney | 525/222 X |
| 3,682,767 | 8/1972 | Britton et al. | 525/222 X |
| 4,032,600 | 6/1977 | MacAdams et al. | 525/222 X |
| 4,116,914 | 9/1978 | Cram et al. | 525/222 X |
| 4,243,576 | 1/1981 | Fischer et al. | 525/222 X |
| 4,266,542 | 5/1981 | Becker et al. | 525/222 X |
| 4,277,578 | 7/1981 | Yoshimura et al. | 525/222 X |
| 4,359,495 | 11/1982 | Schroeder et al. | 525/222 X |
| 4,375,531 | 3/1983 | Ross | 525/222 X |
| 4,376,799 | 3/1983 | Tusim | 604/339 X |
| 4,387,185 | 6/1983 | Schroeder et al. | 525/222 X |
| 4,401,536 | 8/1983 | Tundell et al. | 525/222 X |

FOREIGN PATENT DOCUMENTS

| | | | |
|---|---|---|---|
| 12308 | 11/1983 | Australia . | |
| 3003658 | 8/1981 | Fed. Rep. of Germany | 525/222 |
| 7101400 | 8/1972 | Netherlands | 525/222 |
| 2060652 | 5/1981 | United Kingdom . | |

OTHER PUBLICATIONS

Hawley, Condensed Chemical Dictionary, 9th Ed, p. 362.

Primary Examiner—Nancy A. Swisher
Attorney, Agent, or Firm—John J. Toney; William D. Lee, Jr.; Mark B. Quatt

[57] ABSTRACT

This invention relates to films which have a high degree of silence and pliability and comprise at least one layer formed from a polymeric blend which includes about 40% to 60% by weight of any ethylene and vinyl-acetate copolymer and about 60% to 40% by weight of an elastomeric polyolefin. The elastomeric polyolefin preferably comprises a blend or "alloy" of an ethylene and vinyl-acetate copolymer and an elastomeric ethylene and propylene copolymer. Such films are particularly useful for manufacturing drainage containers or bags for medical applications.

4 Claims, 1 Drawing Figure

SILENT FILM FOR OSTOMY POUCHES

This application is a continuation of application Ser. No. 587,102, filed on Mar. 7, 1984, now abandoned.

This invention relates to the technical field of laminated films and related articles of manufacture, such as bags and containers.

More specifically, the invention concerns films having high degree of noiselessness and pliability, which lend themselves specially well to the manufacture of containers and bags intended for human drainage in medical applications, and particularly for collecting excretion products from patients whose excretive apparatus has been reconstructed surgically.

Easily imagined, and actually readily ascertainable, is the discomfort suffered by patients who, having undergone surgical intervention directed to reconstruct or deviate, albeit in part only, their excretive apparatus following traumatic or pathological events—in particular of the tumoral type—are then obliged to carry along a personal container of excretion products continuously during their active life.

In general, such patients find themselves with an artificial anus formed from a protruding intestinal portion whereto a collecting container is connected which is carried at the waist region close against the skin, under the patient's garments.

There exist a few features that a patient of the kind in question would heartily welcome of such a container, the presence of which container should be desirably pass unnoticed by other persons met in the course of the patient's activities.

Currently available from a number of manufacturers are excretion product collection containers which meet some of the requirements set forth by deviated excretion apparatus patients; these containers, which are formed generally from plastic film materials, exhibit features which could be regarded as reasonably satisfactory for the using patient: among these, mechanical properties may be mentioned which afford a good degree of protection against wear, abrasion, and puncturing, as well as gas and odor barrier properties.

However, and beyond the results achieved thus far, there still exists the need for "concealing from others" in a really effective fashion one's condition of disability. It has been found, in fact, that the use of heretofore commercially available containers makes the patient feel uneasy about such containers emitting, specially as the patient moves around, noise of a low but still audible intensity level.

Furthermore, the containers employed in the past exhibit a texture and "feel" which make them less than ideally suited to applications involving compatibility with human skin, whereby the patent is never allowed to at least occasionally "forget" his/her disabled condition, with obvious disturbing consequences of a psychological nature.

It is an object of this invention, in order to correct such prior deficiencies, to provide a film which, additionally to desirable properties of resistance to wear, abrasion, and puncturing, and as a gas and odor barrier, has improved quietness features characterized by a sound emission of so low an intensity as to be imperceptible to the human ear through most of the audible frequency range.

A further object of this invention is to provide a film as indicated, which is so pliable and soft as to stand comparison with the characteristics of human skin itself.

Another object of the invention, consequent to the former, is to provide bags or containers intended in particular for human draining and collecting excretion products from patients having a deviated reconstructed excretive apparatus, which exhibit high noiselessness and human skin compatibility features.

It has been unexpectedly found that the foregoing objects, and other which will be apparent hereinafter, can be achieved according to the present invention by a film formed from a polymeric blend and characterized in that said polymeric blend includes about 40% to 60% by weight of an ethylene and vinyl-acetate copolymer and about 60% to 40% by weight of an elastomeric polyolefin, said blend imparting the film with high silentness and pliability characteristics.

According to a further aspect of the invention, there are provided drainage containers or bags for medical applications, useful to collect excretion products from patients whose excretive apparatus has been reconstructed and/or deviated, characterized by high noiselessness and pliability properties, as well as by properties of resistance to wear, abrasion, and puncturing, and of gas and odor barrier, said bags or containers being formed from a laminated film which comprises at least one layer comprised of said polymeric blend.

The elastomeric polyolefin used in the polymeric blend intended for preparing the film of this invention, is essentially an "alloy" or blend of two main components: an elastomeric ethylene and propylene (EP) copolymer provided in an amount ranging from 20% to 40% by weight, and an ethylene and vinyl-acetate (EVA) copolymer provided in an amount ranging from 35% to 70% by weight.

The EVA copolymer used in this invention both to make up the elastomeric polyolefin "alloy" and as a component of the polymeric blend, includes preferably 18% to 20% by weight of vinyl-acetate units.

It has been found that films formed from the elastomeric polyolefin having the composition specified above exhibit very high silentness and pliability features as well as excellent mechanical features.

In particular, it has been observed that elastomeric films formed from the elastomeric polyolefin, essentially comprising an alloy of EP and EVA, exhibit high elongation, flexibility, resilience, and a very high impact strength, resistance to puncturing and abrasion, being highly pliable and nontoxic, whereby said elastomeric polyolefin is particularly suitable for preparing films intended for medical applications.

Quite suitable are those elastomeric polyolefins, and alloys of EP or EVA, which have a melting index on the order of 1.5 g/10 min., as measured in accordance with the ASTM D1238 method, a density on the order of 0.94 g/cm|, as measured according to the ASTM D1505 method, and a Shore harness of about 58–68, as measured according to the ASTM D2240 method.

The elastomeric polyolefin entering in the composition of the polymeric blend according to the invention may be prepared with the optional addition of conventional additives for this type of process. Such additives will preferably include fabricability aiding agents, antiblocking agents, flow agents, fillers, etc., and may be added in amounts ranging from 10% to 30% by weight.

The elastomeric copolymer of ethylene/propylene (EP), present in the elastomeric polyolefin in the proportion of 20% to 40% by weight, comprises an ethylene to propylene unit ratio such that the copolymer can have, in fact, the characteristics of an elastomer. In particular, the EP copolymer has an ethylene content in the 55% to 70% ratio by weight.

As a "alloy" composed of elastomeric polyolefin for use in the film of this invention, it would be possible to use a composition like that disclosed, for example, in European Patent Application Publication No. 81300136.9 at page 11.

An unexpected and advantageous aspect of the invention resides in that the above-described elastomeric polyolefin has been found to be readily mixable to the EVA copolymer thanks probably to the fact that its very composition includes the same EVA copolymer. This greatly facilitates the processing operations and affords the possibility of achieving films with the excellent features provided by this invention.

The starting polymeric blend used for preparing the films of this invention may be prepared with conventional methods, effecting, for example, a compounding step through a twin-screw extruder from EVA and granulated elastomeric polyolefin.

To obtain the highly silent and pliable film according to the invention, said polymeric blend, including the EVA-EP alloy and EVA copolymer, may be processed in accordance with conventional industrial practice, e.g. by means of an extruder.

The above-specified additives will promote the fabricability of the blend, which is, however, already possessed of good fabricability features by itself.

Where it is desirable to further control the surface properties, the blend may be additivated with a master batch of the type commonly employed in processing polyethylene polymers.

The film extruded from the polymeric blend as described hereinabove feels to the touch pliable and soft, similarly to human skin, and is virtually free of detectable sound emissions when rubbed.

The film of this invention, for example, allows the rheolar modulus to be lowered considerably with respect to prior films, from a value in the 14 to 16 kg/cm range for a conventional film down to a value in the 5 to 7 kg/cm for the inventive film.

In addition to being silent and pliable, the film of this invention has excellent mechanical characteristics of resistance to wear, abrasion, and puncturing, and can be welded with virtually any of the methods conventionally provided for this purpose.

For special applications, the invention provides for the use of at least one layer comprising said polymeric blend joined or connected to other layers of varying characters, whereby multilayer laminated films are obtained. The character of the additional layers will depend on the intended final use of the multilayer laminated film.

The junction of the layers which make up a multi-layered film comprising at least one layer of polymeric blend, previously described, may be accomplished with traditional methods, such as co-extrusion and lamination with intervening adhesive layers followed by orientation with the trapped bubble technique. An advantageous aspect of the instant invention is that the polymeric blend processing into the final film requires no thermal stabilizers.

One example of such a multilayer film is represented by a film useful in the manufacture of bags or containers intended for draining and/or collecting excretion products from patients whose excretive apparatus has been reconstructed and/or deviated surgically following traumatic or pathological events.

In that case, the final film would be required to posses, in addition to those properties which are typical of the polymeric blend layer—i.e. quietness, pliability, softness, mechanical strength, and good weldability—enhanced gas and odor barrier capabilities. A simple example of a multilayer laminated film having such characteristics comprises a multilayer laminated film of the A/B/A type, where A is a layer of film formed from the polymeric blend including the elastomeric polyolefin (EP+EVA) and the EVA copolymer, and B is a gas and odor barrier layer.

In this case, the overall thickness of the multi-layer laminated film may be, for example, on the order of 75 microns, while the thicknesses of the layer A and layer B may be preferably and approximately in the 22.5 to 32.5 microns range for the layer A, and approximately in the 10 to 30 microns range for the barrier layer B.

Of course, the thicknesses of the layers A and B, and the arrangement and number of the layers may vary somewhat to meet individual requirements.

A gas and odor barrier layer may comprise conventional materials, as normally suitable for the purpose, such as vinylidene chloride copolymers with a comonomer selected from acrylic ester, acrylic acid, and vinylchloride, or an ethylene-vinylalcohol copolymer, or vinylidene flouride-vinyl fluoride copolymer or polyamides, or mixtures thereof, with the optional addition of chlorinated paraffines, stabilizers, and waxes.

Such a multilayer film, and particularly the multilayer film of the A/B/A type described hereinabove, lends itself quite well to the manufacture of containers and bags. Such containers and bags are soft and pliable, produce no perceptible noise, are resistant to thermal and mechanical stresses, and the heat-welded film edges invariably meet the safety requirements imposed on them.

Such bags and containers, when placed in contact with skin, produce no unpleasant feelings; the patent experiences no inconvenience or embarrassment and the absence of noise and rustle effectively makes the presence of the container undetectable.

The example which follows only purports to illustrate the invention and not to restrict its field of application and serves the purpose of emphasizing the degree of effectiveness achieved thereby.

EXAMPLE

A comparative test has been conducted to ascertain the intensity of the sound emissions of some films subjected to rubbing: in particular, the sound emissions have been evaluated respectively from a conventional film, as commercially available and already used for manufacturing drainage containers, and from a film prepared in accordance with this invention.

The conventional film, indicated at C in the accompanying FIG. 1, was CRYOVAC (a registered trademark) MF27 film from W. R. Grace & Co., which comprises the following three layers:

EVA/vinyl chloride-vinylidene chloride (PVDC) copolymer/EVA.

The multilayer film according to this invention, indicated at A-2 in FIG. 1, also comprised three layers (film of the A/B/A type):

the two outward layers A with a thickness of 27.5 microns included each a polymeric blend having the following composition:
50% elastomeric polyolefin having,
  55% EVA (at least 18% vinly-acetate),
  28% EP,
  17% of machinability promoting oil, such that sold by Exxon Chemical Co. under the trademark "FLEXON".
50% EVA (18% vinyl-acetate);
the inward layer B, having a thickness of 20 microns, included vinyl chloride-vinylidene chloride (PVDC) copolymer with 4% chlorinated paraffines and 6% stabilizers and waxes.

The multilayer film according to this invention has been prepared with a hot blown co-extrusion method.

The rheolar modulus of the CRYOVAC (a registered trademark by Grace) film has shown to be equal to 14 kg/cm, whereas for the multilayer film of this invention a considerably lower value of 7 kg/cm has been achieved.

The graph of FIG. 1 shows the intensity in dBA of the sound emitted versus frequency, in the 0–10 kiloHertz range.

It will be apparent from the graph that the film according to the invention shows a marked superiority. The curve A-2, which brings forth the values of intensity of the sound emission from the film A-2, remains, throughout he frequency range (0–10 kH) investigated, below the curve C, which brings forth in plotted form the intensity values for the sound emission from the conventional film C.

In particular, given that most of the sounds below 20 dBA and especially in the range from about 5 to about 8 kiloHertz cannot be perceived by a human ear (reference: Noise Unlimited, Inc., Somerville, N.J., USA), the film A-2 prepared in accordance with this invention shows excellent quietness properties characterized by the emission of sound below the audible threshold.

The pliability and softness properties of the film according to the invention have also been found to provide a particularly pleasant "feel", with a texture comparable to that of human skin.

The added features of resistance to wear, abrasion, and puncturing, as well as gas and odor barrier capabilities, qualify said inventive film for use in the manufacture of containers and bags for medical applications, especially for draining and collecting excretion products form stomized patients.

We claim:

1. A multilayer film from which ostomy pouches or the like having a high degree of silence and pliability may be constructed comprising:
   (a) a barrier layer selected from the group consisting of copolymers of vinylidene chloride and copolymers of ethylene-vinyl alcohol;
   (b) two outer layers with the barrier layer disposed therebetween, each outer layer comprising a blend of:
      (i) 60% to 40% by weight of an elastomeric polyolefin alloy consisting essentially of:
         (1) 20% to 40% by weight of an elastomeric ethylene-propylene copolymer, said copolymer having an ethylene content of 55% to 70% by weight;
         (2) 70% to 35% by weight of a thermoplastic, film forming, ethylenevinyl acetate copolymer having a vinyl acetate content of less than than about 20%; and
         (3) 10% to 30% by weight of said alloy comprising machinability and fabricability promoting agents; and
      (ii) 40% to 60% of a thermoplastic, film forming ethylene-vinyl acetate copolymer having a vinyl-acetate content of less than about 20% by weight; and
   (c) said multilayer film being coextruded and hot blown.

2. The film of claim 1 wherein the elastomeric polyolefin comprises 55% thermoplastic ethylene-vinyl acetate copolymer; 28% elastomeric ethylene-propylene copolymer; and 17% machinability and fabricability promoting agents.

3. The film of claim 2 wherein the outer layer comprises 50% elastomeric polyolefin.

4. The film of claim 3 having a thickness in the range of 22.5 to 32.5 microns.

* * * * *